(12) United States Patent
Okoshi et al.

(10) Patent No.: US 7,691,291 B2
(45) Date of Patent: Apr. 6, 2010

(54) POLYACETYLENE DERIVATIVES

(75) Inventors: Kento Okoshi, Aichi (JP); Eiji Yashima, Aichi (JP)

(73) Assignee: Japan Science and Technology Agency, Saitama (JP)

( * ) Notice: Subject to any disclaimer, the term of this patent is extended or adjusted under 35 U.S.C. 154(b) by 277 days.

(21) Appl. No.: 11/661,721

(22) PCT Filed: Aug. 26, 2005

(86) PCT No.: PCT/JP2005/015507

§ 371 (c)(1),
(2), (4) Date: Feb. 28, 2007

(87) PCT Pub. No.: WO2006/025269

PCT Pub. Date: Mar. 9, 2006

(65) Prior Publication Data

US 2007/0260028 A1    Nov. 8, 2007

(30) Foreign Application Priority Data

Aug. 30, 2004  (JP) .............................. 2004-250238
May 9, 2005    (JP) .............................. 2005-136074

(51) Int. Cl.
*C09K 19/00*    (2006.01)
*C09K 19/06*    (2006.01)
*C09K 19/52*    (2006.01)

(52) U.S. Cl. ............................. 252/299.01; 252/299.6; 428/1.1; 430/20; 430/270.1

(58) Field of Classification Search .................. 430/20, 430/270.1, 1.1, 270; 252/299.01, 299.6; 428/1.1
See application file for complete search history.

(56) References Cited

U.S. PATENT DOCUMENTS 4,615,962 A        10/1986  Garito
2004/0092683 A1     5/2004  Tabata et al.
2007/0145329 A1 *   6/2007  Sakajiri et al. ......... 252/299.01

FOREIGN PATENT DOCUMENTS

WO    WO-01/79311 A1    10/2001

OTHER PUBLICATIONS

Lai et al., PMSE Preprints, 91:589-590 (2004).
Okoshi et al., Macromolecules, 38(10):4061-4064 (2005).
Database WPI Week 199737 - Thomson Scientific. London. GB AN 1997-399561, XP002555073 & JP 09176243 A (Aug. 7, 1997).

* cited by examiner

*Primary Examiner*—Geraldina Visconti
(74) *Attorney, Agent, or Firm*—Peter F. Corless; Christine C. O'Day; Edwards Angell Palmer & Dodge LLP

(57) ABSTRACT

Novel optically active polyacetylene derivatives exhibiting liquid crystallinity; liquid crystal compositions containing the derivatives; and moldings thereof. Specifically, polyacetylene derivatives which have helical structure of rigid-rod shape and which exhibit a liquid crystal phase either in a solvent containing an organic solvent as the main component or in a molten state as well as electric field orientation; liquid crystal compositions containing the derivatives; and moldings thereof. More specifically, polyacetylene derivatives having helical structure of rigid-rod shape as represented by the general formula [1]; liquid crystal compositions containing the derivatives; and moldings thereof: wherein $R^1$ and $R^2$ are each independently aminocarbonyl of an amino acid having an ester linkage with $C_{2-22}$ alkyl or carbonylamino of an amino acid having an amide linkage with $C_{2-22}$ alkyl, the amino acid being achiral one, or chiral one of (S)- or (R)-configuration, or a racemic mixture composed of both antipodes; and X is a number satisfying the relationship: $0 < X \leqq 1$.

10 Claims, 9 Drawing Sheets

Platinum Electrode

POLYACETYLENE DERIVATIVES

TECHNICAL FIELD

The present invention relates to novel polyacetylene derivatives which have helical structure of rigid-rod shape and which exhibit a cholesteric liquid crystal phase or a nematic liquid crystal phase.

BACKGROUND ART

As an example of a polymer having helical structure of rigid-rod shape, a polyglutamic acid comprising a long n-alkyl chain, for example, n-decyl group, has been reported by Watanabe, et al. (see Non-Patent Literature 1, Non-Patent Literature 2, Non-Patent Literature 3, Non-Patent Literature 4, etc.).

In addition, in this connection, it has been reported that in a polyglutamic acid comprising a long chain alkyl group of n-decyl group or longer, not only cholesteric liquid crystal property but also hexagonal columnar and smectic phases are observed.

Further, it has been also reported that some other rigid or semi-rigid polymers, which are cellulose, polyisocyanate, polysilane and wholly aromatic polymer, exhibit thermotropic liquid crystallinity and lyotropic liquid crystallinity, as well as the above polyglutamic acid.

As another example of a liquid crystalline polymer having rigid-rod helical structure as described above, which has a great dipole moment along main chains of the polymer due to hydrogen bond between amide groups in a molecule, a polypeptide has been known. As an example of a polymer whose main chains are oriented by means of application of electric field by utilizing this great dipole moment, poly(γ-benzyl-L-glutamate) has been known (see Non-Patent Literatures 5 to 7).

In addition, in Patent Literature 1, a compound of 4-ethylenyl-benzoyl-L-glutamic acid which is useful as an intermediate for producing a compound of N-[2-amino-4-substituted-[(pyrrolo or pyrido)[2,3-d]pyrimidinyl-alkyl]benzoyl]-L-glutamic acid having an inhibitory effect to a dehydrofolic acid reducing enzyme, has been disclosed.

Patent Literature 1: JP-A-6-25246
Non-Patent Literature 1: Macromolecules, 17, 1004 (1984)
Non-Patent Literature 2: Macromolecules, 18, 2141 (1985)
Non-Patent Literature 3: Mol. Cryst. Liq. Cryst., 164, 135 (1988)
Non-Patent Literature 4: Springer-Verlag, Berlin, Heidelberg, p. 99-108 (1994)
Non-Patent Literature 5: E. Iizuka, et al., Biochemica et Biophysica Acta, 175 (2), 457-459 (1969)
Non-Patent Literature 6: E. Iizuka, et al., Biochemica et Biophysica Acta, 243 (1), 1-10 (1971)
Non-Patent Literature 7: E. Iizuka, et al., J. Phys. Soc. Jpn., 34 (4), 1054-1058 (1973)

DISCLOSURE OF THE INVENTION

Problem to be Solved by the Invention

The inventors of the present invention began the study considering that some of polyacetylene derivatives having an optically active side chain of helical structure might have useful liquid crystal characteristics due to the twisted structure thereof, from the comparison with the structure in the polymers having the above rigid-rod helical structure. Therefore, an object of the present invention is to provide novel optically active polyacetylene derivatives exhibiting liquid crystalinity, and further to provide liquid crystal compositions based on the liquid crystal characteristics endemic to said polymers.

In addition, another object of the present invention is to provide polyacetylene polymers having helical structure which integrate a great dipole moment in the main chain direction, and further, to provide polyacetylene polymers which are capable of orienting main chains thereof in response to application of electric field.

Means for Solving the Problem

The present invention relates to polyacetylene derivatives, which have rigid-rod helical structure and exhibit liquid crystal phase in a solution containing an organic solvent as a main component thereof.

Further, the inventors of the present invention considered that it might be possible to form a structure of rigid-rod shape and integrate a great dipole moment in the main chain direction by introducing an amide group into their structures and mutually forming hydrogen bond, also in the polyacetylene polymers having helical structure, from the comparison with the structure in the aforementioned polymers. And the inventors have found out rigid-rod polyacetylene polymers, which are capable of orienting main chains thereof in response to application of electric field.

Consequently, the present invention relates to polyacetylene derivatives which have rigid-rod molecular shape and exhibit a high degree of polymer chain orientation with application of an electric field in a solution or in a molten state, more specifically, polyacetylene derivatives which have rigid-rod molecular shape and exhibit a high degree of polymer chain orientation with application of an electric field in a solution or in a molten state, characterized in that hydrogen bond is formed between neighboring amide groups in a side chain.

More specifically, the present invention relates to the above polyacetylene derivatives having rigid-rod helical structure, represented by the following general formula [1]:

[Chemical Formula 3]

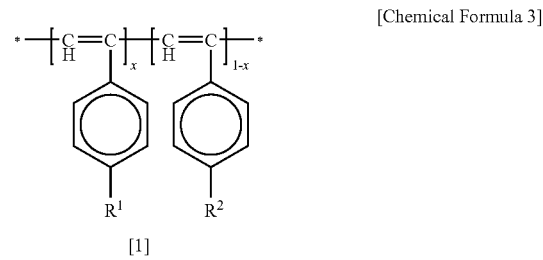

(Chemical Formula [1])

[wherein each of $R^1$ and $R^2$ independently represents aminocarbonyl group of an amino acid having an ester linkage with $C_2$-$C_{22}$ alkyl group, or carbonylamino group of an amino acid having an amide linkage with $C_2$-$C_{22}$ alkyl group, said amino acid being achiral, or (S) chiral configuration and/or (R) chiral configuration, or a racemic mixture composed of (S) and (R); and X represents a number satisfying $0<X\leq 1$].

In addition, the present invention relates to liquid crystal compositions comprising the above polyacetylene derivatives.

Further, the present invention relates to solids comprising the above polyacetylene derivatives in which the structure of liquid crystal phase is immobilized by evaporating a solvent, preferably films which have a membranous form.

Furthermore, the present invention relates to acetylene derivative monomers represented by the following general formula [2]:

[Chemical Formula 4]

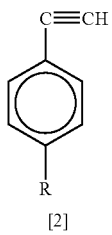

[2]

(Chemical Formula [2])

[wherein R represents aminocarbonyl group of an amino acid having an ester linkage with $C_2$-$C_{22}$ alkyl group, or carbonylamino group of an amino acid having an amide linkage with $C_2$-$C_{22}$ alkyl group, said amino acid being achiral, or (S) chiral configuration and/or (R) chiral configuration, or a mixture composed of (S) and (R); and X represents a number satisfying $0<X\leq1$].

The present invention will be further explained in detail, but the present invention should not be limited to the specific embodiments described below.

The inventors of the present invention have intensively persevered the study considering that since polyglutamic acid mentioned in the aforementioned conventional technology builds up a rigid-rod shape indispensable for expressing liquid crystallinity by strong intramolecular hydrogen bond, polyacetylene derivatives, which have optically active side chains of helical structure, may express high rigidity by introducing an amino acid having hydrogen-bond-forming property into side chains thereof, and found that this structure has unexpectedly a rigid-rod helical structure and quite unique characteristics, that is, liquid crystal characteristics, and accomplished the present invention.

This liquid crystal phase was expressed in almost all organic solvents excluding alcohols or in the mixtures thereof, and it was cholesteric phase when the side chain was chiral, and nematic phase when the side chain was racemic or achiral. These cholesteric and nematic liquid crystallinities are brought by constitution characterizing chemical structures of the above polyacetylene derivatives.

Further, the inventors of the present invention considered that since polyglutamic acid mentioned in the above conventional technology builds up a rigid-rod shape by strong intramolecular hydrogen bond and integrates a great dipole moment in the main chain direction, polyacetylene derivatives having helical structure, may also be able to express rigid-rod shape and a great dipole moment in the main chain direction by introducing an amino acid having hydrogen-bond-forming property into side chains thereof. In the polyacetylene derivatives introduced with amino acid having hydrogen-bond-forming property into side chains thereof, it had been considered that a state in which each dipole is antiparallel to each other is energetically more stable because each of two side chains projected out to the opposite direction from each other form hydrogen bond with side chains in the upper and lower positions thereof (Macromolecules, 36, 561-564 (2003)). Namely, it had been considered that such a polyacetylene derivatives do not have a macroscopic dipole moment in the main chain direction. However, after intensive study, the inventors of the present invention have found that this structure has unexpectedly rigid-rod helical structure and thereby extremely unique characteristics, that is, electric field orientation property due to the great dipole moment in the main chain direction. This highly orienting property of main chains of the polymer could be immobilized easily by evaporating a solvent or cooling to the glass transition point or below.

Thus, the inventors of the present invention have found that due to the formation of hydrogen bond by the amide group on the side chains of the rigid-rod helical polymer between the neighboring side chains, every carbonyl group on the side chains faces in the main chain direction of the polymer, and a great dipole moment can be integrated in this direction. Due to rigid-rod polymer, not only the polymer can form cholesteric and nematic liquid crystal phases in a solution or in a molten state, but also this great dipole moment can align in response to electric field applied to the liquid crystal phase to form a state in which main chains of the polymer are highly oriented. In addition, a further feature of the present invention is that the oriented structure of this highly oriented liquid crystalline polyacetylene can be immobilized as a film by evaporating a solvent or cooling to the glass transition point or below.

Such structure of the present invention, in which main chains of the polymer are highly oriented, can be immobilized easily by evaporating a solvent or cooling to the glass transition point or below, and applications to anisotropic conductive film, variable retardation film, chemical substance recognizing sensor, high-density recording device, and the like can be considered, and these molecular elements can be produced simply at low cost without a large-sized production facility. Also, it has been found that such molecule has a viscosity index of at least 0.8 when measured in a chloroform solution (0.1 to 0.2 g/vol %) at 30° C., and a persistence length of over 10 nm (for measurement method, see Examples, etc. described later).

The inventors of the present invention completed the present invention based on finding that the rigid-rod helical polyacetylene derivatives, which exhibit cholesteric phase or nematic phase of anisotropic liquid having a structure of micrometer to nanometer scale formed by self-organization of the helical rigid-rod polymer.

One of great features of the present invention is that the liquid crystal structure of liquid crystalline polyacetylene derivatives can be immobilized as a membranous form (film), and further that planar orientation thereof is also easy due to planar orientation effect based on rigidity of the molecule.

"Rigid-rod" means such a state that the above polyacetylene derivatives exhibit a viscosity index ($\alpha$) (specific measurement method will be described later) of at least 0.8 or above, preferably 0.9 or above, and more preferably 1.0 or above when measured, for example, in a chloroform solution (0.1 to 0.2 g/vol %) at 30° C., and a calculated persistence length of at least 10 nm or above, and preferably over 15 nm. The cholestric and nematic liquid crystallinities are brought by a constitution characterizing the chemical structure of the above polyacetylene derivatives.

These structures of nanometer scale, which are formed voluntarily, can be easily immobilized by evaporating the solvent thereof, and thereby a membranous solid film and the like comprising the polyacetylene derivatives represented by the above general formula [1] having an immobilized structure of liquid crystal phase can be obtained.

In this connection, since the above liquid crystal phase expresses in almost all organic solvents excluding alcohols or a mixture thereof, an example of solvent to be used involves almost all organic solvent excluding alcohols.

The aminocarbonyl group of an amino acid having an ester linkage with $C_2$-$C_{22}$ alkyl group shown by $R^1$ and $R^2$ in the polyacetylene derivatives represented by the above general formula [1] and R in the acetylene derivative monomers represented by the above general formula [2] is a group where the carboxyl group in an amino acid, preferably an α-amino acid is esterified with a $C_2$-$C_{22}$ alkyl group and the amino group is carbonylated. Also, the "carbonylamino group" of an amino acid having an amide linkage with $C_2$-$C_{22}$ alkyl group shown by $R^1$ and $R^2$ in the polyacetylene derivatives represented by the above general formula [1] and R in the acetylene derivative monomers represented by the above general formula [2] is a group where the amino group in an amino acid, preferably an α-amino acid is amidated with a carbonyl group (acyl group) having a $C_2$-$C_{22}$ alkyl group and the carboxyl group binds to the nitrogen atom of said amido group in the amidated state.

These groups are represented by the following formulae, respectively. The aminocarbonyl group of an amino acid is a moiety represented by the following formula:

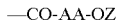

—CO-AA-OZ (wherein -AA- represents an amino acid moiety where hydrogen atom of the amino group and hydroxyl group of the carboxyl group are excluded; the left side part of AA represents the amino group side of amino acid, and the right side part of AA represents carboxyl group side of amino acid. Z represents alkyl group having 2 to 22 carbon atoms, preferably 2 to 18 carbon atoms, 3 to 22 carbon atoms, 3 to 18 carbon atoms, 6 to 22 carbon atoms, 6 to 18 carbon atoms, 8 to 22 carbon atoms, or 8 to 18 carbon atoms). The carbonylamino group of an amino acid is a moiety represented by the following formula:

Z—CO-AA-NH—

(wherein, -AA- represents an amino acid moiety where hydrogen atom of the amino group and hydroxyl group of the carboxyl group are excluded; the left side part of AA represents the amino group side of amino acid, and the right side part of AA represents carboxyl group side of amino acid. Z represents alkyl group having 2 to 22 carbon atoms, preferably 2 to 18 carbon atoms, 3 to 22 carbon atoms, 3 to 18 carbon atoms, 6 to 22 carbon atoms, 6 to 18 carbon atoms, 8 to 22 carbon atoms, or 8 to 18 carbon atoms).

In the polyacetylene derivatives represented by the above general formula [1], the $C_2$-$C_{22}$ alkyl group in the aminocarbonyl group of an amino acid having an ester linkage with $C_2$-$C_{22}$ alkyl group and the $C_2$-$C_{22}$ alkyl group in the carbonylamino group of an amino acid having an amide linkage with $C_2$-$C_{22}$ alkyl group shown by $R^1$ and $R^2$ include, for example, alkyl group having 2 to 22 carbon atoms such as ethyl, propyl, isopropyl, butyl, isobutyl, sec-butyl, tert-butyl, pentyl, hexyl, heptyl, octyl, nonyl, decyl, dodecyl, tetradecyl, pentadecyl, hexadecyl, octadecyl, eicosyl, docosyl, and the like. Among these $C_2$-$C_{22}$ alkyl groups, more preferably one includes, for example, an alkyl group having 8 to 22 carbon atoms or 8 to 18 carbon atoms such as octyl, decyl, dodecyl, pentadecyl, octadecyl, and the like.

In addition, the amino acid in the amino acid having an ester linkage with $C_2$-$C_{22}$ alkyl group and the amino acid in the amino acid having an amide linkage with $C_2$-$C_{22}$ alkyl group is preferably α-amino acid, and more preferably hydrophobic α-amino acid. The amino acid of the present invention may be natural type one or non-natural type one, but is preferably natural type one in view of easy procurement. The amino acid of the present invention may be achiral, or (S) chiral configuration and/or (R) chiral configuration, or a mixture composed of (S) and (R). When the amino acid is a mixture, the mixture is preferably a racemic mixture composed of (S)- and (R)-antipodes in equal amounts. The hydrophobic α-amino acid includes an α-amino acid to which a hydrophobic group such as alkyl group having 1 to 10, preferably 1 to 5 carbon atoms; aryl group having 6 to 20, preferably 6 to 14 carbon atoms; aralkyl group having 7 to 30, preferably 7 to 18 carbon atoms; heterocyclic group such as indolyl group; the groups substituted by a substituent having no active hydrogen atom such as methylsulfide on those groups; or the like is bound at the α-carbon atom of the α-amino acid. Preferable hydrophobic α-amino acid includes an amino acid selected from the group consisting of alanine, valine, leucine, isoleucine, phenylalanine, tryptophan, methionine, proline, and the like. Specific examples of these amino acids include, but are of course not limited to, for example, L(S)-, D(R)- or racemic alanine, L(S)-, D(R)- or racemic valine, L(S)-, D(R)- or racemic isoleucine, methylalanine, L(S)-, D(R)- or racemic leucine, phenylalanine, L(S)-, D(R)- or racemic methionine, or the like.

In the acetylene derivative monomers represented by the above general formula [2], the $C_2$-$C_{22}$ alkyl group in the aminocarbonyl group of an amino acid having an ester linkage with $C_2$-$C_{22}$ alkyl group and the $C_2$-$C_{22}$ alkyl group in the carbonylamino group of an amino acid having an amide linkage with $C_2$-$C_{22}$ alkyl group both represented by R are exactly same one to those in the above $R^1$ and $R^2$, and the more preferable alkyl group is also exactly same to them.

In addition, the amino acid having an ester linkage with $C_2$-$C_{22}$ alkyl group and the amino acid having an amide linkage with $C_2$-$C_{22}$ alkyl group in R are also exactly same to those in the above $R^1$ and $R^2$, with the proviso that the case when the amino acid is a glutamic acid is excluded.

Number average molecular weight of the polyacetylene derivatives represented by the above general formula [1] according to the present invention is preferably 10,000 or above, and more preferably 50,000 or above.

Further, degree of polymerization is 30 or above, preferably 60 or above, and more preferably 150 or above.

X in the above general formula [1] represents molar fraction of each monomer in the polyacetylene derivative, which is composed of a phenylacetylene derivative monomer having substituent $R^1$ and a phenylacetylene derivative monomer having substituent $R^2$, and total of both molar fractions is 1. The substituents $R^1$ and $R^2$ may be the same, and in that case, the polymer becomes a homopolymer. When the substituents $R^1$ and $R^2$ are different from each other, the polymer becomes a copolymer, and said copolymer may be a random copolymer or a block copolymer.

Accordingly, X in the above general formula [1] becomes a value more than 0 and less than 1. When X is 1, the polymer becomes a homopolymer of the phenylacetylene derivative monomer having substituent $R^1$. When a value of X is less than 1, the polymer becomes a copolymer of a phenylacetylene derivative monomer having substituent $R^1$ and a phenylacetylene derivative monomer having substituent $R^2$.

Specific examples of the polyacetylene derivatives represented by the above general formula [1] include, for example, polyacetylene derivative having an aminocarbonyl group of an amino acid having an ester linkage with $C_2$-$C_{22}$ alkyl group as a substitutent at the 4-position such as L(S)-, D(R)- or racemic poly[4-(decyloxyalanylcarbamoyl)phenylacetylene], L(S)-, D(R)- or racemic poly[4-(decyloxyvalinylcarbamoyl)phenylacetylene], L(S)-, D (R)- or racemic poly[4-

(decyloxyisoleucinylcarbamoyl)phenylacetylene], poly[4-(decyloxymethylalanylcarbamoyl)phenylacetylene], and the like; and for example, polyacetylene derivative having a carbonylamino group of an amino acid having an amide linkage with $C_2$-$C_{22}$ alkyl group as a substituent at the 4-position such as L(S)-, D(R)- or racemic poly [4-(N-decylcarbonylalanylamide)phenylacetylene], L(S)-, D(R)- or racemic poly [4-(N-decylcarbonylvalinylamide)phenylacetylene], L(S)-, D(R)- or poly[4-(N-decylcarbonylisoleucinylamide)phenylacetylene], L(S)-, D(R)- or racemic [4-(N-decylcarbonylmethylalanylamide)phenylacetylene], and the like, but the polyacetylene derivatives according to the present invention are of course not limited to them.

Specific examples of the acetylene derivative monomers represented by the above general formula [2] include, for example, phenylacetylene derivative having an aminocarbonyl group of an amino acid having an ester linkage with $C_2$-$C_{22}$ alkyl group as a substituent at the 4-position such as L(S)-, D(R)- or racemic 4-(decyloxyalanylcarbamoyl)phenylacetylene, L(S)-, D(R)- or racemic 4-(decyloxyvalinylcarbamoyl)phenylacetylene, L(S)-, D(R)- or racemic 4-(decyloxyisoleucinylcarbamoyl)phenylacetylene, 4-(decyloxymethylalanylcarbamoyl)phenylacetylene, and the like, and for example, phenylacetylene derivative having a carbonylamino group of an amino acid having an amide linkage with $C_2$-$C_{22}$ alkyl group as a substituent at the 4-position such as L(S)-, D(R)- or racemic 4-(N-decylcarbonylalanylamide)phenylacetylene, L(S)-, D(R)- or racemic 4-(N-decylcarbonylvalinylamide)phenylacetylene, L(S)-, D(R)- or racemic 4-(N-decylcarbonylisoleucinylamide)phenylacetylene, 4-(N-decylcarbonyl-methylalanylamide)phenylacetylene, and the like, but the acetylene derivative monomers according to the present invention are of course not limited to them.

Specific examples of the acetylene derivative monomers represented by the above general formula [2] are illustrated by the structural formulae as shown below.

4-(Decyloxy-L-alanylcarbamoyl)phenylacetylene

[Chemical Formula 5]

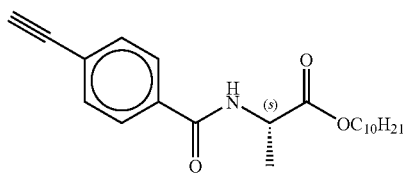

(Chemical Formula)
4-(Decyloxy-L-valinylcarbamoyl)phenylacetylene

[Chemical formula 6]

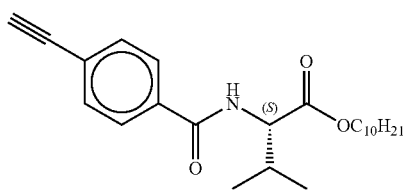

(Chemical Formula)
4-(Decyloxy-L-isoleucinylcarbamoyl)phenylacetylene

[Chemical formula 7]

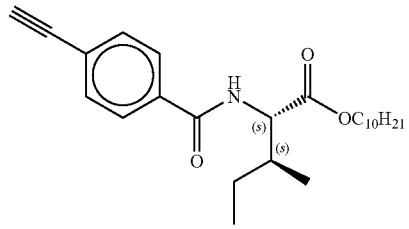

(Chemical Formula)
4-(Decyloxy-methylalanylcarbamoyl)phenylacetylene

[Chemical formula 8]

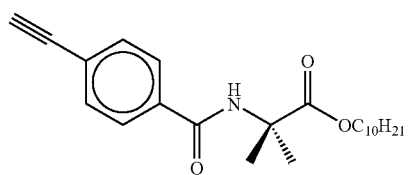

(Chemical Formula)
4-(N-decylcarbonyl-L-alanylamide)phenylacetylene

[Chemical formula 9]

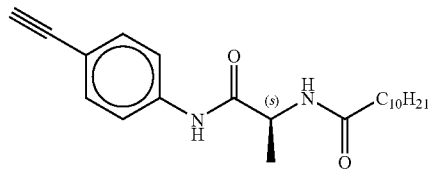

(Chemical Formula)
4-(N-decylcarbonyl-L-valinylamide)phenylacetylene

[Chemical formula 10]

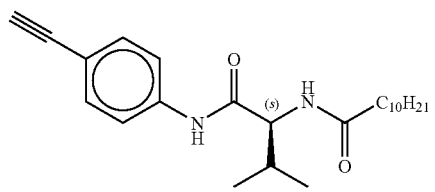

(Chemical Formula)

4-(N-decylcarbonyl-L-isoleucylamide)phenylacetylene

[Chemical formula 11]

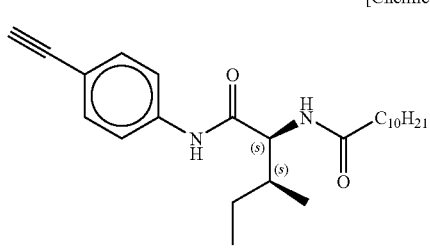

(Chemical Formula)

4-(N-decylcarbonyl-methylalanylamide)phenylacetylene

[Chemical formula 12]

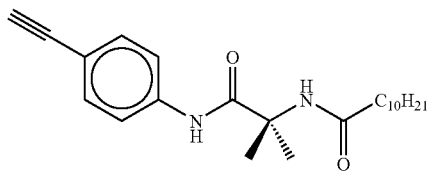

(Chemical Formula)

The acetylene derivative monomers represented by the above general formula [2] can be easily synthesized using 4-substituted acetylene derivative such as 4-ethynylbenzoic acid or 4-ethynylaniline or the like, according to the common process for peptide synthesis.

Namely, for example, a 4-substituted acetylene derivative such as 4-ethynylbenzoic acid or 4-ethynylaniline or the like is reacted with ($C_2$-$C_{22}$) alkyl ester of an amino acid such as decyl ester of, for example, L(S)-, D(R)- or racemic alanine or the like, or ($C_2$-$C_{22}$) alkylamide of an amino acid such as dodecylamide of L(S)-, D(R)- or racemic isoleucine or the like, in a solvent such as dimethylacetamide, in the presence of a dehydrating condensing agent such as N,N'-dicyclohexylcarbodiimide or the like, if necessary, in the coexistence of N-hydroxysuccineimide or 1-hydroxybenzotriazole, and the like to inhibit recemization, for example, at room temperature for several to over ten hours, followed by being reacted at 100° C. or higher, for example, 120° C. for one to several hours, if necessary, to complete the reaction. After completion of the reaction, insoluble matter is filtered off according to the common method, and the product is isolated and purified by a silica gel column chromatography or the like, and recrystallized from hexane or the like, if necessary, to yield easily the desired product, for example, 4-ethynylbenzoylalanine decyl ester or 4-ethynylphenylisoleucine dodecylamide and the like.

The polyacetylene derivative represented by the above general formula [1] can be easily obtained by homopolymerizing or copolymerizing one or two kinds of the acetylene derivative monomers represented by the above general formula [2] according to the common method.

Namely, one or two kinds of the acetylene derivative monomers represented by the above general formula [2] may be subjected to polymerization reaction, under the atmosphere of an inert gas such as, for example, argon gas or nitrogen gas, or the like, in a solvent such as, for example, anhydrous tetrahydrofuran (THF) and the like, in the coexistence of amines such as, for example, anhydrous triethylamine and the like, in the presence of a transition metal complex catalyst such as, for example, bis(1,5-cyclooctadiene)rhodium dichloride, bis(norbornadiene)rhodium dichloride, and the like, at around 30° C. for several hours, and after completion of the reaction, according to the common method, the reaction liquid is poured into an organic solvent such as methanol, ethanol, and the like, which does not dissolve the polymer produced, to precipitate the polymer produced, and isolating by means of centrifugation or the like then drying the polymer to obtain the desired polyacetylene derivative represented by the above general formula [1].

In order to explain characteristics of the polyacetylene derivatives of the present invention more specifically, the polyacetylene derivatives of the present invention will be explained referring to poly[(S)-(+)-4-(decyloxyalanylcarbamoyl)phenylacetylene] (hereinafter, abbreviated as Polymer S) and poly[(R/S)-(±)-4-(decyloxyalanylcarbamoyl)phenylacetylene] (hereinafter, abbreviated as Polymer R/S) as examples.

The viscosity index in the present invention means an index represented by α in the following Mark-Houwink-Sakurada's formula:

$$[\eta]=K[M]^\alpha$$

which is a value to quantify a macroscopic shape of the polymer in a solution. The value of around 0.5 to 0.6 represents a shape of random coil, and the value of 0.8 or above, preferably 0.9 or above represents a rigid-rod shape. In the formula, η means intrinsic viscosity of a polymer, M means weight average molecular weight, and K is a constant.

In addition, a relationship between molecular weight and intrinsic viscosity can be measured, for example, by the GPC-VISCO method (Gel Permeation Chromatograph-Viscometer Method). The GPC-VISCO method is a kind of liquid chromatography where polymer chains are separated depending on difference in molecular size (hydrodynamic volume). This is a technique to measure limiting viscosity and difference in refractive indices of a polymer solution, which is size-dependently fractionated by GPC, by incorporating a viscometer (VISCO) and a differential refractometer (RI), by varying retention volume, and to calculate sequentially limiting viscosity, molecular weight and polymer content of the polymer solution, and to obtain finally information on molecular weight characteristics and viscosity characteristics of the polymer material.

Molecular weight-intrinsic viscosity relationships obtained by the GPC-VISCO method for chloroform solutions of the polymer S and the polymer R/S of the present invention both having number average molecular weights of about 230,000 are shown in FIG. 6. In FIG. 6, the horizontal axis represents weight average molecular weight in logarithmic scale, and the vertical axis represents intrinsic viscosity in logarithmic scale. As a result, viscosity indices of the polymer S and the polymer R/S measured at 30° C. were 1.18 and 0.96, respectively. These results clearly show that both of the polymer S and the polymer R/S have rigid-rod shape, and prove such presumption that the polymer R/S has a structure in which a right and a left helical main chain are contained in equal amounts.

In addition, the persistence length means an index which has a unit of distance expressing rigidity of a polymer. A usual random coil polymer has a value of 2 to 3 nm. For the polymer S and the polymer R/S, both of which have number average molecular weights of about 230,000 by the helical wormlike model based on a result of the aforementioned GPC-VISCO method, persistence lengths thereof were calculated and resulted in 36.9 nm and 16.1 nm, respectively, and it was revalidated that these polymers have main chains of very rigid shapes.

The liquid crystal phase of the polyacetylene derivatives of the present invention can be verified, for example, by a polarized-light micrograph in the case of dichloroethane solution or in the case molded to a film.

For example, polarized-light micrographs of the polymer S and the polymer R/S of the present invention both having number average molecular weights of about 230,000 in dichloroethane solutions are shown in FIG. 7 and FIG. 8, respectively. In the case of the polymer S, a typical striped pattern of optical texture called as fingerprint pattern was observed in a reproducible fashion. This is an optical texture characteristic to the cholesteric liquid crystal phase. Contrary to this, in the case of the polymer R/S, a typical optical texture called as schlieren texture was observed in a reproducible fashion. This is an optical texture characteristic to the nematic liquid crystal phase. In addition, FIG. 9 shows a transmission electron micrograph for a thin tissue of film sample prepared by evaporating the solvent from a dichloroethane solution of the polymer S. A clear striped texture is observed, indicating that the macroscopic helical structure of the cholesteric liquid crystal phase has been immobilized in the solid.

As a method for verifying formation of hydrogen bond between the amide groups on the side chains in the polyacetylene derivatives of the present invention, for example, an IR absorption spectrum (IR) can be used. Firstly, an absorption derived from stretching vibration of the carbonyl group in the side chain ester at the wave number of around 1,748 $cm^{-1}$ and an absorption derived from stretching vibration of the carbonyl group in the side chain amide group at the wave number of around 1,635 $cm^{-1}$ of the polyacetylene derivatives of the present invention in a non-polar solvent are measured. Thereafter, the above absorption bands are measured in a polar solvent, which is thought to inhibit formation of hydrogen bond, to be able to verify changes in the absorption wave numbers. The non-polar solvent to be used here includes hydrocarbon type solvents such as benzene and the like, and the polar solvent to be used includes ether type solvents such as THF and the like.

The verification for the formation of hydrogen bond between the amide groups on the side chain will be explained using the polymer S having a number average molecular weight of about 460,000 as an example, referring to the IR chart of FIG. 10. In the IR chart of FIG. 10, the horizontal axis expresses wave number ($cm^{-1}$), and the vertical axis expresses absorbance. On this axis, upper scale shows greater absorbance. FIG. 10 shows absorptions of the cases in 100% benzene (solid line), benzene/THF=75/25 (fine dotted line), benzene/THF=50/50 (thick dotted line), benzene/THF=25/75 (thick dashed line), and 100% THF (dashed line). From these results, an increase of the absorption band for non-hydrogen bonded carbonyl group of the amide group at around 1,665 $cm^{-1}$ with increase of concentration of THF is observed, indicating that the hydrogen bond is inhibited. Namely, it can be understood that almost all amidecarbonyl groups of the amide group form the hydrogen bond in a benzene solution, whereas almost all carbonyl groups are inhibited to form the hydrogen bond in 100% THF solution.

The polyacetylene derivatives of the present invention express a rigid-rod shape and a great dipole moment in the main chain direction, because the derivatives have a rigid-rod helical structure and a hydrogen-bond-forming amino acid have been introduced in the side chains thereof. And, the derivatives have electric field orientation property due to this great dipole moment in the main chain direction. Further, the high degree of the polymer main chain orientation in the polyacetylene derivatives of the present invention can be easily immobilized by evaporating a solvent or cooling to the glass transition point or below, and therefore can be molded to film or the like. In the polyacetylene derivatives of the present invention molded into film or the like in such way, practical standard value of parallelism degree in orientation of the polymer main chains (the polyacetylene skeleton in polymer) can be obtained, for example, by measuring a half width ($H°$) of an intensity distribution measured along the Debye ring (also referred to as Debye-Scherrer ring) of reflection derived from a distance between polymer chains.

"Practical standard value of parallelism degree in orientation: Π" in the present invention is defined by the following formula:

$$\Pi = (180° - H°)/180°$$

(wherein $H°$ represents a half width of intensity distribution measured along the Debye ring of reflection derived from a distance between polymer chains, and Π represents a practical standard value of parallelism degree in orientation.)

(Masao Kakudo et al., "X-Ray Diffraction of Polymers", Maruzen, p 188).

Molded articles (solid) such as film and the like of the preferable polyacetylene derivatives of the present invention have a value of "practical standard value of parallelism degree in orientation: Π" of 0.8 or above, preferably 0.85 or above, and more preferably 0.9 or above.

For example, a wide angle X-ray photograph of the polymer S having a number average molecular weight of about 460,000 is shown in FIG. 11 instead of drawing. Also, an intensity distribution measured along the Debye ring of reflection derived from a distance between polymer chains of the same polymer S is shown in FIG. 12. In FIG. 12, the horizontal axis expresses angle, and the vertical axis expresses absorbance. The above angle was determined based on the direction of the platinum electrode as shown in FIG. 13. As a result, the practical standard value of parallelism degree in orientation of this polyacetylene derivative was calculated as 0.92.

EFFECT OF THE INVENTION

By using the polyacetylene derivatives having a rigid-rod helical structure of the present invention, a cholesteric phase that is a micrometer to nanometer scale of structure formed by self-organization of the helical rod-like polymer or a nematic phase that is anisotropic liquid can be expressed in an organic solvent, and these nanometer scale of structure formed voluntarily can be easily immobilized by evaporating the solvent. One of great features of the liquid crystalline polyacetylene derivatives of the present invention is that the liquid crystal structure can be immobilized as a membranous form (film) and that planar orientation is also easy due to the planar orientation effect based on the rigidity of the molecule.

In addition, the present invention is based on a discovery of the fact that due to formation of hydrogen bond between neighboring side chains by amide groups on side chains of a helical rigid-rod polymer, every carbonyl group on the side chains faces in the main chain direction of the polymer, to integrate a great dipole moment along this direction. Due to the rigid-rod shape thereof, this polymer forms a cholestiric or nematic phase in a solution or in a molten state. And by applying electric field to the liquid crystal phase, this great dipole moment aligns in response to this electric field to form a state in which main chains of the polymer are highly oriented. Further, another feature of the present invention is that the oriented structure of the highly oriented liquid crystalline polyacetyene can be immobilized as a film by evaporating a solvent or cooling to the glass transition point or below.

The polyacetylene derivatives of the present invention having a structure in which main chains of the polymer are highly oriented can be easily immobilized by evaporating a solvent or cooling to the glass transition point or below, and the immobilized solid, for example, film, is thought to be utilized to anisotropic conductive film, variable retardation film, chemical substance recognizing sensor, high-density recording device, and the like, and further, these molecular elements can be produced simply and at low cost without a large sized manufacturing facility.

Accordingly, the liquid crystalline polyacetylene derivatives according to the present invention and solids immobilized the liquid crystal structure exhibit significant effects on the points that they can be widely applied as optical materials, and applications, for example, to circularly-polarized filters for IR rays of 1,550 nm and 1,300 nm which are used for optical communication, variable retardation film, chemical substance recognition sensor and high-density recording device are expected, and that these molecular elements can be produced simply at low cost without a large sized manufacturing facility.

BEST MODE FOR CARRYING OUT THE INVENTION

Figure 1:
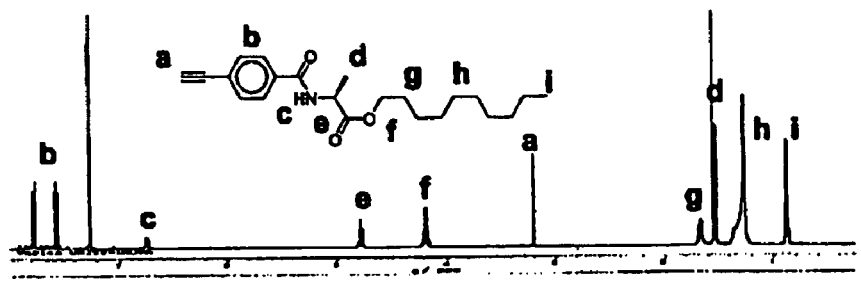
FIG. 1 is a $^1$H NMR spectrum chart of (S)-(+)-4-(decyloxyalanylcarbamoyl)phenylacetylene (Example 1), which is an acetylene derivative monomer according to the present invention.

Hereinafter, the present invention will be explained more specifically referring to Examples, but the present invention is not limited by these Examples in any way.

EXAMPLE 1

Preparation of (S)-(+)-4-[(1-decyloxycarbonyl-1-ethylamino) carbonyl]phenylacetylene[(S)-(+)-4-[(decyloxyalanylcarbamoyl)phenylacetylene]

Into a solution of 4-ethynylbenzoic acid (0.293 g, 2.01 mmol) in anhydrous dimethylacetamide, 1-hydroxybenzotriazole (0.307 g, 2.01 mmol) and N,N'-dicyclohexylcarbodiimide (0.426 g, 2.07 mmol) were added, and the solution was stirred under the nitrogen stream at 0° C. for 1 hour then at room temperature for further 1 hour. After that, (S)-(+)-decylalaninate (0.488 g, 2.13 mmol) was added thereto and stirred at room temperature for 3 hours then at 120° C. for further 3 hours. After completion of the reaction, insoluble matter was filtered off, and the solvent was distilled off under the reduced pressure from the resulting filtrate to obtain residue, which was isolated and purified by a silica gel chromatography (eluant: chloroform/ethyl acetate), then recrystallized from hexane to yield the titled acetylene derivative monomer (0.33 g) according to the present invention as a crystalline solid. Yield: 45%.

$^1$H NMR (500 MHz, CDCl$_3$, room temperature) δ:
0.88 (t, 3H; CH$_3$), 1.21-1.29 (m, 14H; CH$_2$), 1.52 (d, 3H; CH$_3$), 1.63-1.68 (m, 2H; CH$_2$), 4.15-4.21 (m, 2H; CH$_2$), 4.75-4.78 (m, 1H; CH), 6.72 (d, 1H; NH), 7.53 (d, 2H; aromatic), 7.80 (d, 2H; aromatic).

The above $^1$H NMR spectrum chart is shown in FIG. 1.

$^{13}$C NMR (500 MHz, CDCl$_3$, room temperature) δ:
14.04, 18.78, 22.69, 25.90, 28.67, 29.24, 29.31, 29.54, 29.55, 31.93, 48.82, 65.92, 79.49, 82.87, 125.77, 127.07, 132.38, 134.29, 165.96, 173.24.

Figure 2:
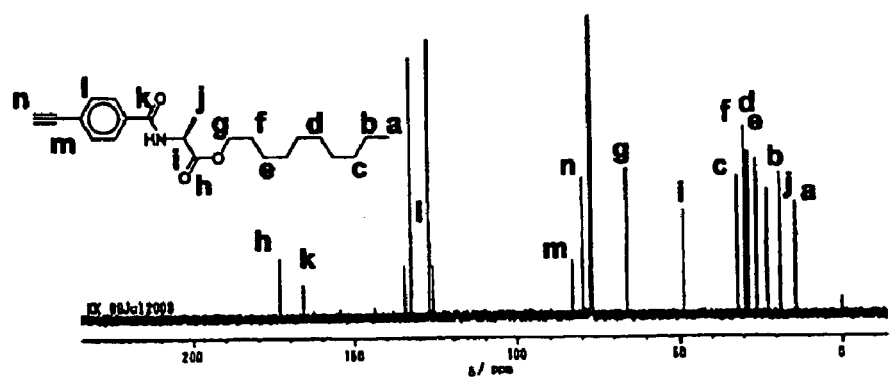
FIG. 2 is a $^{13}$C NMR spectrum chart of (S)-(+)-4-(decyloxyalanylcarbamoyl)phenylacetylene (Example 1), which is an acetylene derivative monomer according to the present invention.

The above $^{13}$C NMR spectrum chart is shown in FIG. 2.

Elemental Analysis
Calculated value (for $C_{22}H_{31}NO_3$=357.5) (%):
C, 73.91; H, 8.74; N, 3.92.
Observed value (%):
C, 73.83; H, 8.80; N, 3.92.

EXAMPLE 2

Preparation of (R/S)-(±)-4-(decyloxyalanylcarbamoyl)phenylacetlene

Exactly the same reaction and post-treatments were repeated as in Example 1 except that (R/S)-(±)-decylalaninate (0.488 g, 2.13 mmol) was used instead of using (S)-(+)-decylalaninate (0.488 g, 2.13 mmol) in Example 1, to obtain the titled compound with the same yield as in Example 1.

Various spectral data and results of elemental analysis thereof were almost same as in Example 1.

EXAMPLE 3

(1) Preparation of the Polyacetylene Derivatives According to the Present Invention In a dry polymerization tube (50 ml), (S)-(+)-4-(decyloxyalanylcarbamoyl)phenylacetylene or (R/S)-(±)-4-(decyloxyalanylcarbamoyl)phenylacetlene (100 mg, 0.28 mmol) as a starting monomer was placed, and the tube was sufficiently deaerated, then purged with nitrogen. After that, anhydrous tetrahydrofuran (THF) (300 µl) and anhydrous triethylamine (100 µl) were added and dissolved by stirring. Then, a solution of norbornadiene rhodium dichloride (7.45 mg, 0.028 mmol) in anhydrous THF was added to said monomer solution at room temperature so that concentrations of the monomer and the catalyst became 0.5 M and 0.05 M, respectively, and the reaction liquid was stirred at 30° C. for 3 hours under the nitrogen atmosphere to promote the reaction. After completion of the reaction, the reaction liquid was poured into a large amount of ethanol, and the generated precipitate was separated by centrifugation, then vacuum-dried for 5 hours. The precipitate was dissolved in benzene and subjected to freeze dry to obtain poly[(S)-(+)-4-(decyloxyalanylcarbamoyl)phenylacetylene] (hereinafter, abbreviated as Polymer S) or poly[(R/S)-(±)-4-(decyloxyalanylcarbamoyl)phenylacetlene] (hereinafter, abbreviated as Polymer R/S). The number average molecular weights of the resulting polymers were about 230,000.

$^1$H NMR (500 MHz, $CDCl_3$, 55° C.) δ:
0.86 (singletlike, 3H; $CH_3$), 1.05-1.40 (singletlike, 14H; $CH_2$), 1.5 (broad, 3H; $CH_3$), 1.6 (broad, 2H; $CH_2$), 4.1 (broad, 2H; $CH_2$), 4.7 (broad, 1H; CH), 6.1 (broad, 1H; =CH), 6.8 (broad, 2H; aromatic), 7.5 (broad, 2H; aromatic).

Figure 3:
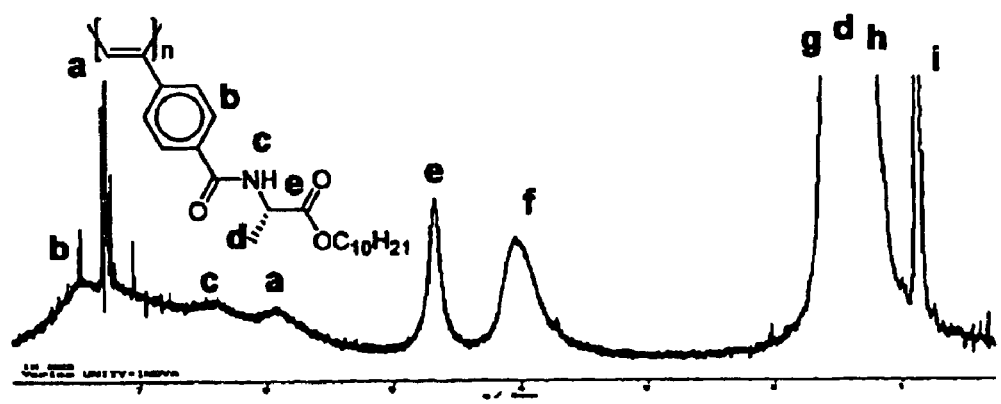
FIG. 3 is a $^1$H NMR spectrum chart of poly[(S)-(+)-4-(decyloxyalanylcarbamoyl)phenylacetylene] (Example 3-(1)), which is a polyacetylene derivative according to the present invention.

The above $^1$H NMR spectrum chart is shown in FIG. 3.

$^{13}$C NMR (500 MHz, $CDCl_3$, 55° C.) δ: 14.04, 18.02, 22.68, 25.96, 28.69, 29.33, 29.60, 31.94, 48.71, 65.47, 127.40, 132.79, 167.00, 173.23.

Figure 4:
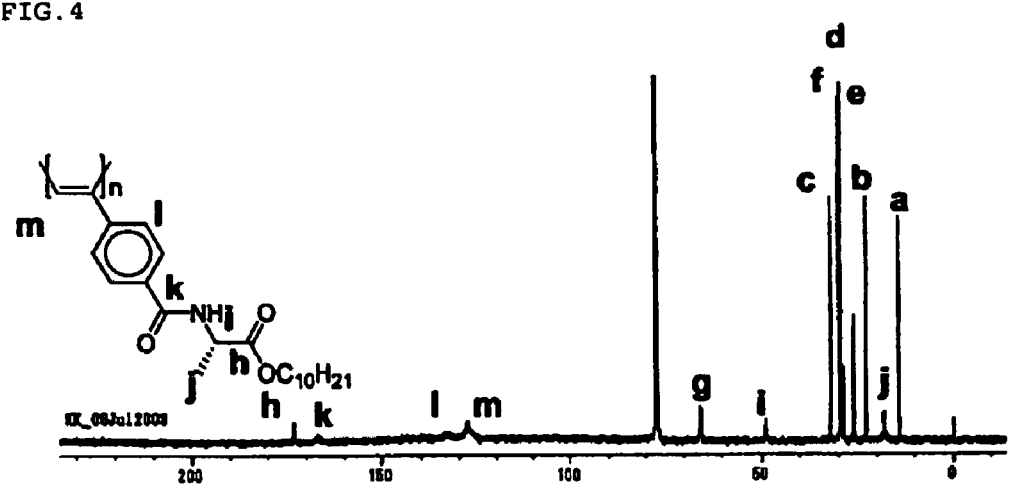
FIG. 4 is a $^{13}$C NMR spectrum chart of poly[(S)-(+)-4-(decyloxyalanylcarbamoyl)phenylacetylene] (Example 3-(1)), which is a polyacetylene derivative according to the present invention.

The above $^{13}$C NMR spectrum chart is shown in FIG. 4.

Elemental Analysis
Calculated value (for $C_{22}H_{31}NO_3$: 357.5) (%):
C, 73.91; H, 8.74; N, 3.92.
Observed value (%):
C, 73.18; H, 8.69; N, 3.84.

(2) Verification of Formation of Main Chain Helical Structure

Figure 5:
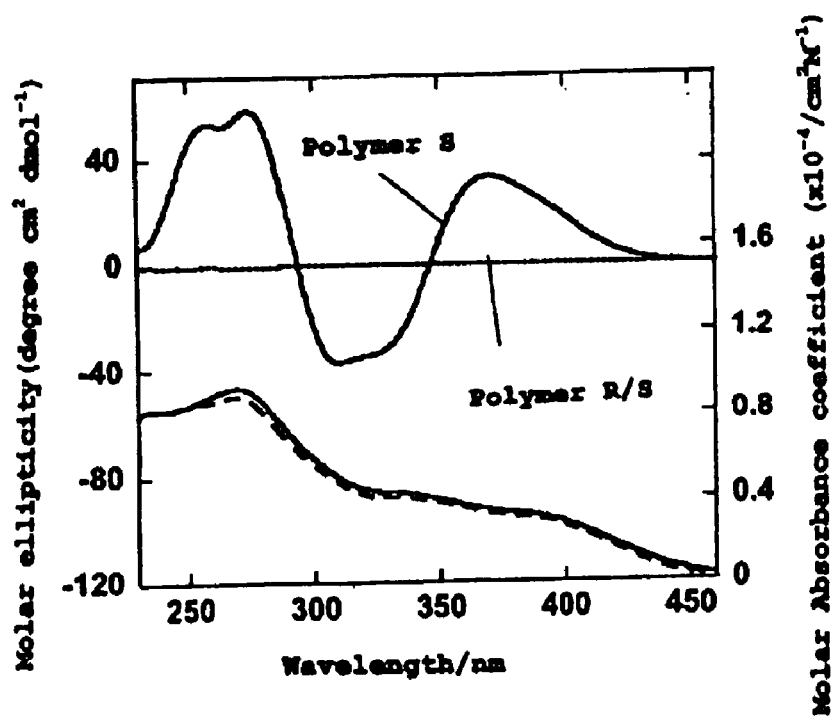
FIG. 5 shows circular dichroism (CD) spectra and UV-Visible absorption spectra of the polymer S and the polymer R/S according to the present invention (see Example 3-(2)).

Each of the polymer S (1.5 mg) and the polymer R/S (1.5 mg) was dissolved in chloroform (1 mL), and circular dichroism spectra (CD) and UV-V absorption spectra thereof were measured. As a result, a split type CD spectrum derived from main chain of the polymer was observed in the range of wavelength of 300 to 500 nm for the polymer S, but no CD signal was observed for the polymer R/S. These results are shown in FIG. 5.

From these results, it was verified that a chiral main chain helical structure was induced in the polymer S having a chiral molecular structure.

In the case of the polymer R/S, from the fact that the UV-Visual absorption spectrum thereof is almost same to that of the polymer S having a chiral main chain helical structure, it is considered that the polymer may be not in a form of a random coil but in a state containing right and left main chain helical structures in equal amounts.

Consequently, a molecular weight-intrinsic viscosity relationships were obtained by the GPC-VISCO method (Gel Permeation Chromatograph-Viscometer method) to determine viscosity indices and persistence lengths of said polymers. In this connection, viscosity index means an index represented by α in the following Mark-Houwink-sakurada's formula:

$$[\eta]=K[M]^\alpha$$

which is a value to quantify a macroscopic shape of the polymer in a solution. The value of around 0.5 to 0.6 represents a shape of random coil, and the value of 0.9 or above represents a rigid-rod shape. In the above formula, η means intrinsic viscosity of the polymer, M means weight average molecular weight, and K is a constant. Also, persistence length is an index having a unit of distance expressing rigidity of the polymer, and has a value of 2 to 3 nm for a usual random coil polymer.

The GPC-VISCO method (Gel Permeation Chromatograph-Viscometer method) is a kind of liquid chromatography where polymer chains are separated depending on difference in molecular size (hydrodynamic volume). This is a technique to measure limiting viscosity and difference in refractive indices of a polymer solution, which is size-dependently fractionated by GPC, by incorporating a viscometer (VISCO) and a differential refractometer (RI), by varying retention volume, and calculating sequentially limiting viscosity, molecular weight and polymer content of the polymer solution, to obtain finally information on molecular weight characteristics and viscosity characteristics of the polymer material.

In this connection, measuring conditions in the Examples are as follows.

GPC: HLC-8220GPC Gel Permeation Chromatography (GPC) (produced by Toso Co., Ltd.)

Column: TS gel Multipore HXL-M (length: 30 cm, 2 pieces) (produced by Toso Co., Ltd.)

Solvent: Chloroform (produced by Wako Pure Chemical Industries, Ltd.)

Flow rate: 1.0 mL/min

Temperature: 30° C.

Concentration of sample: 0.15 w/v %

Injection amount: 100 µl.

Figure 6:
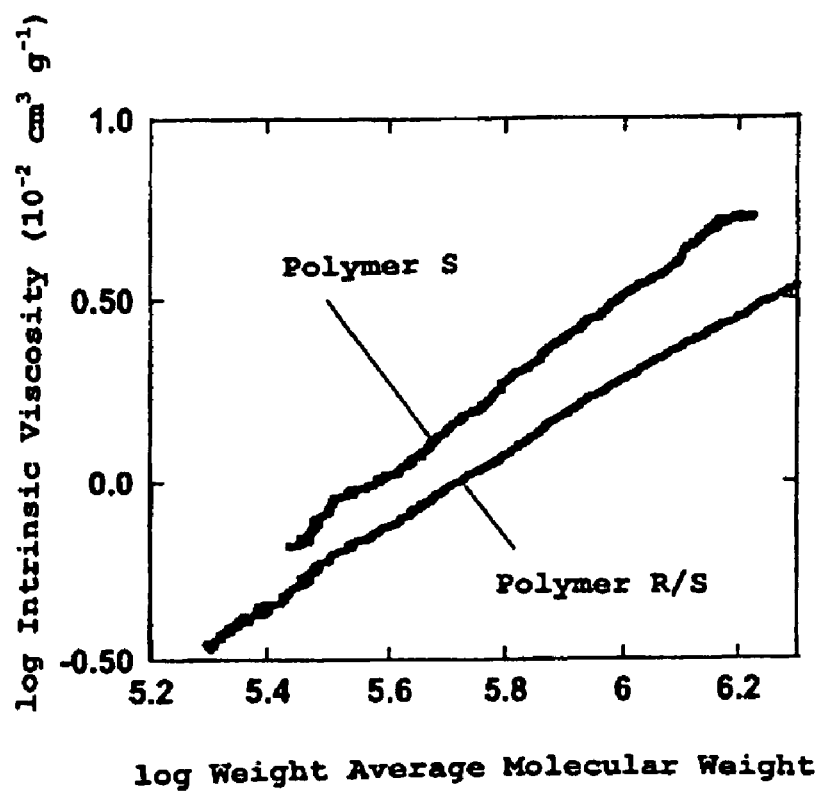
FIG. 6 shows Mark-Houwink-Sakurada plots of the polymer S and the polymer R/S according to the present invention (see Example 3-(2)).

The molecular weight-intrinsic viscosity relationships obtained for the polymer S and the polymer R/S are shown in FIG. 6. From these results, the viscosity indices of the polymer S and the polymer R/S measured at 30° C. were found to be 1.18 and 0.96, respectively. These results clearly show that both of the polymer S and the polymer R/S have rigid-rod shape, and prove the presumption that the polymer R/S is in a state containing right and left main chain helical structures in equal amounts.

Further, based on these experimental results, persistence length of each of the polymer S and the polymer R/S was calculated according to the helical wormlike model, and found to be 36.9 nm and 16.1 nm, respectively, revalidating that the main chains were in a very rigid shape.

(3) Identification of Lyotropic Liquid Crystal Phases Appeared

Figure 7:
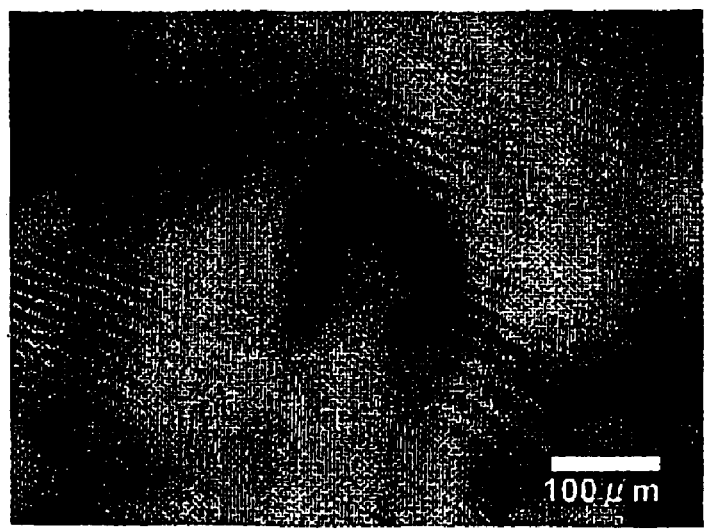
FIG. 7 shows a polarized-light micrograph of the polymer S according to the present invention in 20% by weight dichloroethane solution instead of drawing (see Example 3-(3)).
Figure 8:
FIG. 8 shows a polarized-light micrograph of the polymer R/S according to the present invention in 20% by weight dichloroethane solution instead of drawing (see Example 3-(3)).

Polarized-light micrographs of 20% by weight dichloroethane solutions of the polymer S and the polymer R/S samples are shown in FIG. 7 and FIG. 8, respectively. In the case of the polymer S, a typical striped optical texture called as fingerprint pattern was observed in a reproducible fashion. This is an optical texture characteristic to the cholesteric liquid crystal phase. Contrary to this, in the case of the polymer R/S, a typical optical texture called as schlieren texture was observed in a reproducible fashion. This is an optical texture characteristic to the nematic liquid crystal phase.

Figure 9:
FIG. 9 shows a transmission electron micrograph of a thin tissue sample of solidified polymer S obtained by evaporating the solvent from a 20% by weight dichloroethane solution of the polymer S according to the present invention instead of drawing (see Example 3-(3)).

FIG. 9 is a transmission electron micrograph for a thin tissue of membranous solid sample prepared by evaporating a solvent from a dichloroethane solution of the polymer S to solidify said polymer. A clear striped texture is observed, indicating that the macroscopic helical structure of the cholesteric liquid crystal phase has been immobilized in a solid.

EXAMPLE 4

Preparation of 4-ethynylbenzoyl-L-alanine Decyl Ester as a Starting Monomer

Into a solution of 4-ethynylbenzoic acid (0.293 g, 2.01 mmol) in dimethylacetamide in a dry three-necked flask (100 mL), 1-hydroxybenzotriazole (0.307 g, 2.01 mmol) and N,N'-dicyclohexylcarbodiimide (0.426 g, 2.07 mmol) were added and dissolved by stirring the mixture on an ice bath. L-decylalaninate (0.488 g, 2.13 mmol) was added thereto, and the solution was stirred at room temperature for 3 hours then at 120° C. for further 1 hour. After the solution was cooled to room temperature, precipitate was filtered off, and the product was isolated by column chromatography using silica gel.

EXAMPLE 5

Preparation of poly(4-ethynylbenzoyl-L-alanine Decyl Ester) (Hereinafter, Referred to as Polymer L1)

[Chemical Formula 13]

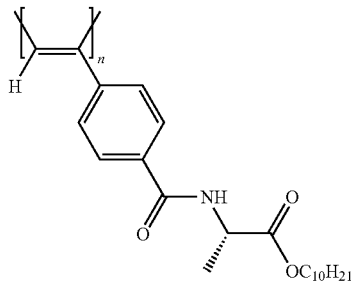

(Chemical Formula of Polymer L1)

In a dry polymerization tube (50 ml), 4-ethynylbenzoyl-L-alanine decyl ester (100 mg) as a starting monomer obtained in Example 4 was placed, and the tube was sufficiently deaerated, then purged with argon gas. After that, anhydrous THF (300 μL) and anhydrous triethylamine (100 μL) were added and dissolved by stirring. Then, a solution (56 μL) of bis (norbornadiene) rhodium dichloride (11.5 mg, produced by Aldrich Corp.) in anhydrous THF (1 mL) was added to said monomer solution, and the reaction liquid was stirred at 30° C. for 3 hours under the nitrogen atmosphere to promote the reaction. After completion of the reaction, the reaction liquid was added dropwise to methanol, and the precipitate formed was separated by centrifugation at 3,000 rpm. The solution of the precipitate in benzene was subjected to freeze dry to obtain poly(4-ethynylbenzoyl-L-alanine decyl ester) (Polymer L1). The number average molecular weight of the resulting polymer was about 460,000.

Verification of Hydrogen Bond Formation Between Amide Groups on the Side Chains of the Polymer L1

Figure 10:
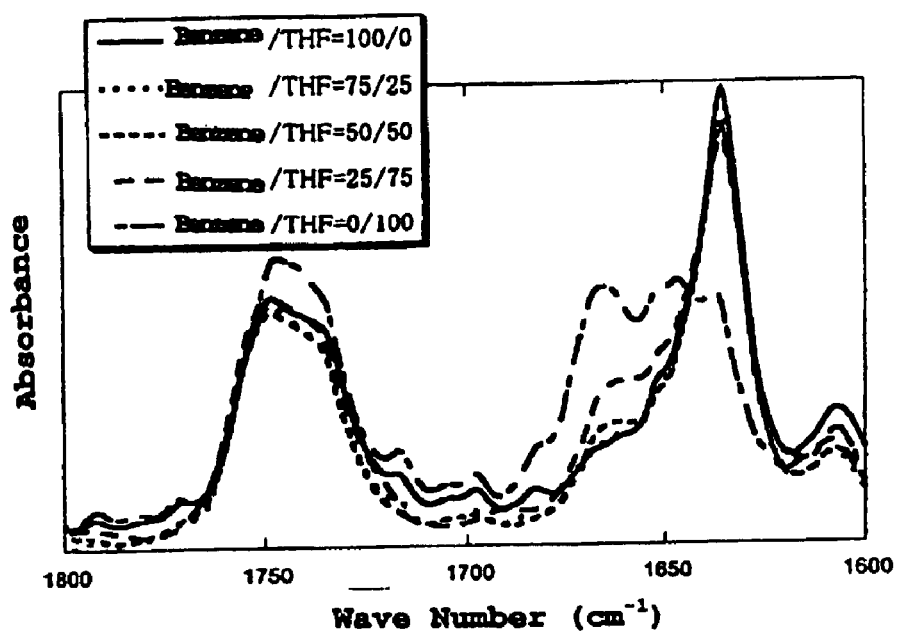
FIG. 10 shows charts of IR absorption spectra (IR) of the polymer L1 (Example 5) of the present invention in benzene, THF and mixtures thereof.

The polymer L1 (1.5 mg) was dissolved in benzene (0.2 mL), and the solution was injected into a sealed cell using $CaF_2$ as a window material to measure an IR absorption spectrum. An absorption derived from stretching vibration of the carbonyl group in the ester on the side chains was observed at the wave number of around 1,748 $cm^{-1}$, and another absorption derived from stretching vibration of the carbonyl group in the amide groups on the side chains was observed at the wave number of around 1,635 $cm^{-1}$. In order to clarify whether these carbonyl groups are involved in the hydrogen bond, solutions of the polymer L1 in benzene mixed with THF that was thought to be a polar solvent to inhibit hydrogen bond formation, were prepared to measure IR absorption spectra thereof. These results are shown in FIG. 10. With increase of the concentration of THF, increase of the non-hydrogen-bond-forming absorption band of carbonyl group in the amide groups is observed at the wave number of around 1,665 $cm^{-1}$, indicating that the hydrogen bond is inhibited. Namely, in the benzene solution, almost all amide-carbonyl groups form the hydrogen bond, whereas in the solution of the polymer L1 in 100% THF, almost all carbonyl groups are inhibited to form the hydrogen bond.

Figure 13:
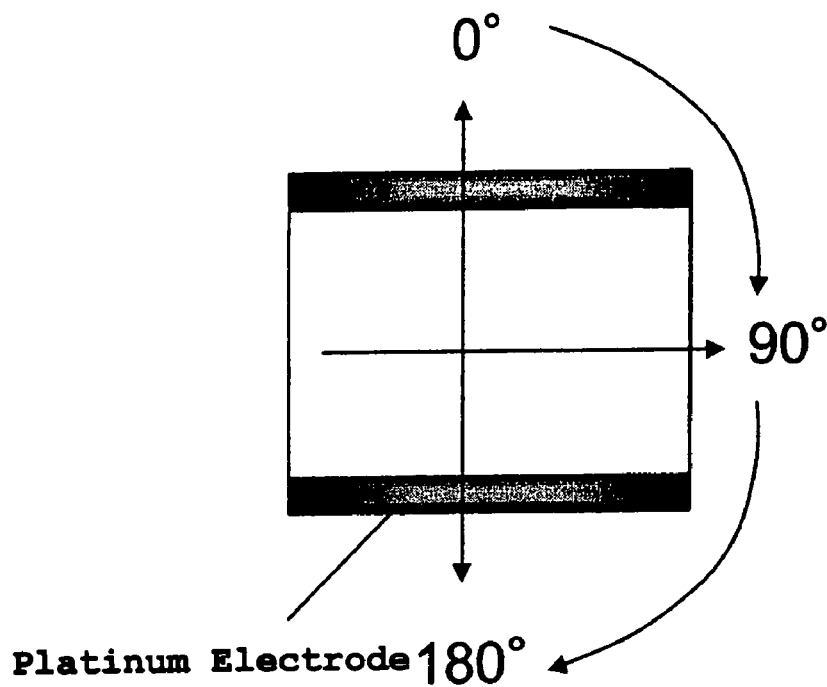
FIG. 13 shows a relationship between electric field and measurement angle.
Figure 14:
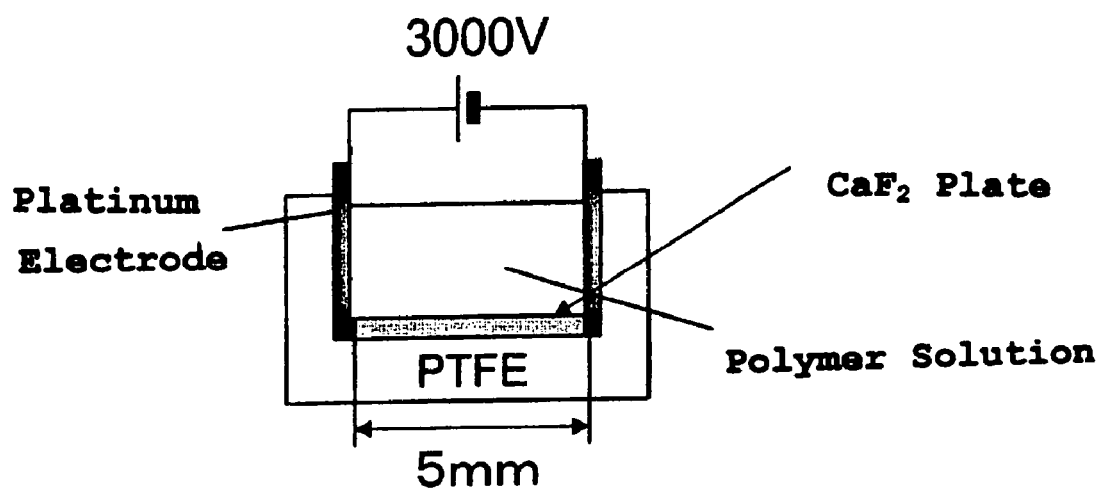
FIG. 14 is a pattern diagram of an electric-field-orienting cell used for electric field orientation of the polymer L1 (Example 5) of the present invention.
Figure 15:
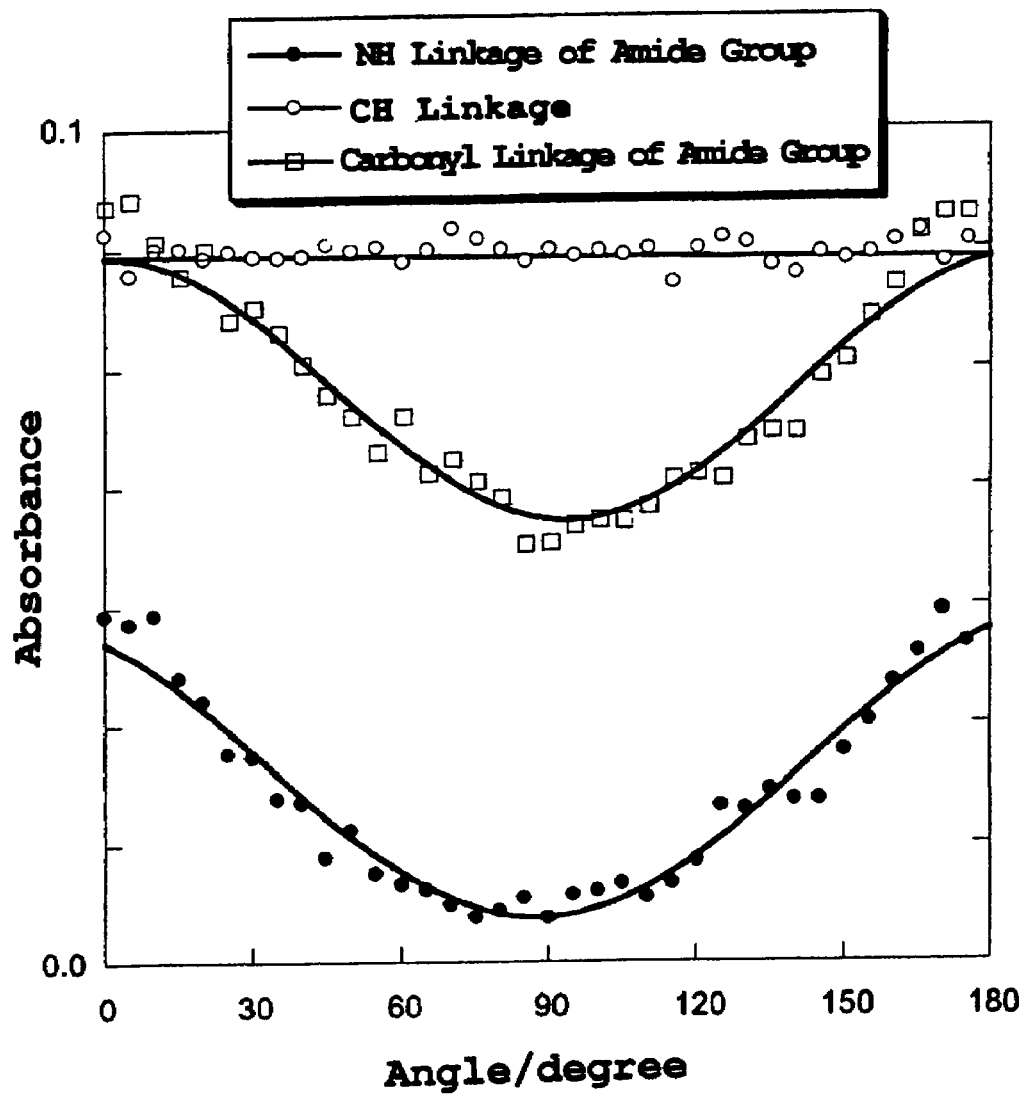
FIG. 15 shows results of measurement on dependencies on the direction of the plane of polarized-light of absorption band intensities of carbonyl group, N—H group and C—H group in the amide group of the electric-field-oriented film from a benzene solution of the polymer L1 (Example 5) of the present invention.

Verification of Orientation of Main Chains of the Polymer by Applying Electric Field to a Solution of the Polymer L1 in Benzene A 2% by weight solution (0.5 mL) of the polymer L1 in benzene was poured into a cell having a width of 5 mm shown in FIG. 14, and benzene was slowly evaporated under the atmosphere of benzene vapor while a voltage of 3,000 V was applied between the platinum electrodes. After benzene was completely evaporated to form a polymer film on the $CaF_2$ plate, measurement of polarized IR absorption spectrum was conducted. Dependencies of absorption band intensities of carbonyl group, N—H group and C—H group of the amide groups on the plane of polarization are shown in FIG. 15. In FIG. 15, the horizontal axis expresses angle, and the vertical axis expresses absorbance. Setting of the angle in the horizontal axis is same to that shown in FIG. 13. In FIG. 15, black dot symbol (●) shows NH linkage in the amide group, open circle symbol (○) shows CH linkage, and open square symbol (□) shows carbonyl linkage in the amide group. The plane of polarization is set in such way that the application direction of electric field corresponds to 0° and 180°. From these results, it is understood that the carbonyl group and the N—H group in the amide groups are strongly oriented in the application direction of electric field, whereas the C—H group is not oriented at all and isotropic.

Figure 16:
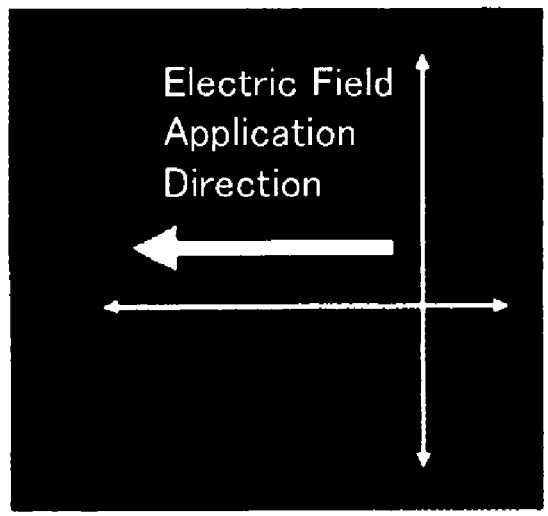
FIG. 16 shows a color photograph of a polarized-light microgram of an electric-field-oriented film from a benzene solution of the polymer L1 (Example 5) of the present invention instead of drawing.
Figure 16:
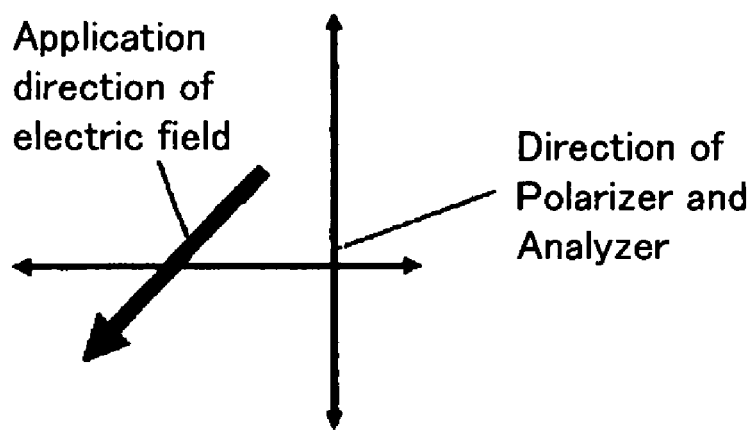
Figure 16:
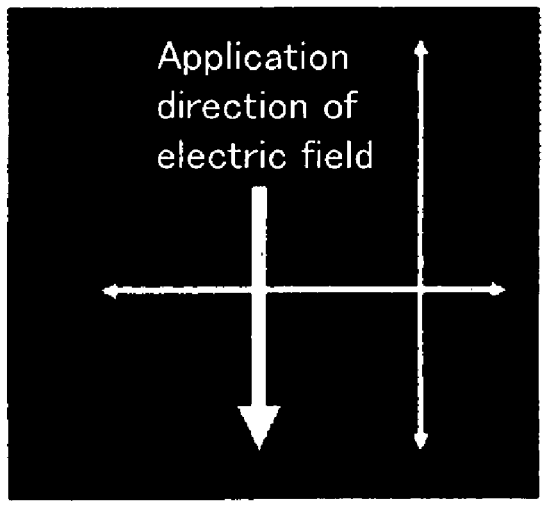

In FIG. 16, a color photograph of a polarized-light microgram of this $CaF_2$ plate is shown instead of drawing. The thick arrow symbol in FIG. 16 shows a application direction of electric field, and the orthogonal two arrow symbols show directions of a polarizer and an analyzer. The three photographs in FIG. 16 illustrate states in which an oriented sample (on the rotating stage) is rotated by 0 degree, 45 degrees and 90 degrees under the polarizing microscope while the orthogonal polarizer is fixed as it is. Generally, the retardation axis (an axis of greater refractive index) of an index ellipsoid corresponds to main chain direction of the polymer, and it is known that under the orthogonal polarizer, light does not pass through when this axis coincides with the polarizing direction of the polarizer or the analyzer, whereas transmission amount of light due to birefringence becomes the maximum when this axis is at just 45° to them. In FIG. 16, since light transmits when the application direction of electric field was set at just 45° to the polarization direction of the polarizer or the analyzer, and light did not transmit when the application direction of electric field coincides with the polarization direction of the polarizer or the analyzer, it was verified that main chains of the polymer was oriented along the application direction of electric field. Namely, since the extinction position is shown when the application direction of electric field coincides with the polarization direction of the polarizer or the analyzer, it is understood that main chain of the polymer is strongly oriented along the application direction of electric field.

Measurement of Practical Standard Value of Parallelism Degree in the Orientation of Polymer Main Chains in the Electric-Field-Oriented Film From half width of an intensity distribution measured along the Debye ring of reflection derived from a distance between polymer chains obtained by X-ray diffraction experiment, practical standard value (Masao Kakudo et al., "X-Ray Diffraction of Polymers", Maruzen, p 188) of parallelism degree in orientation calculated according to the following formula was measured:

$$\Pi = (180° - H°)/180°$$

(wherein $H°$ represents a half width of intensity distribution measured along the Debye ring of reflection derived from a distance between polymer chain, and n represents a practical standard value of parallelism degree in orientation).

Figure 11:
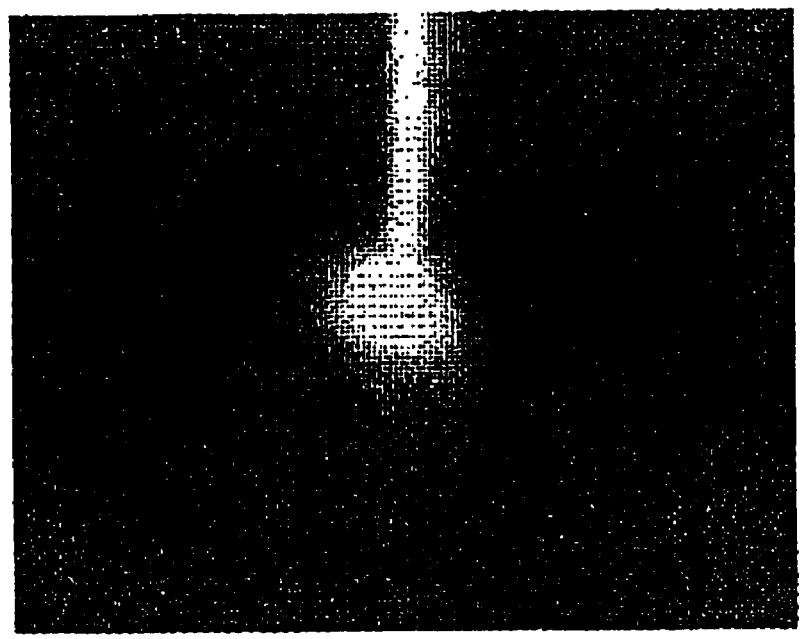
FIG. 11 shows a wide angle X-ray photograph of an electric-field-oriented film of the polymer L1 (Example 5) of the present invention instead of drawing.
Figure 12:
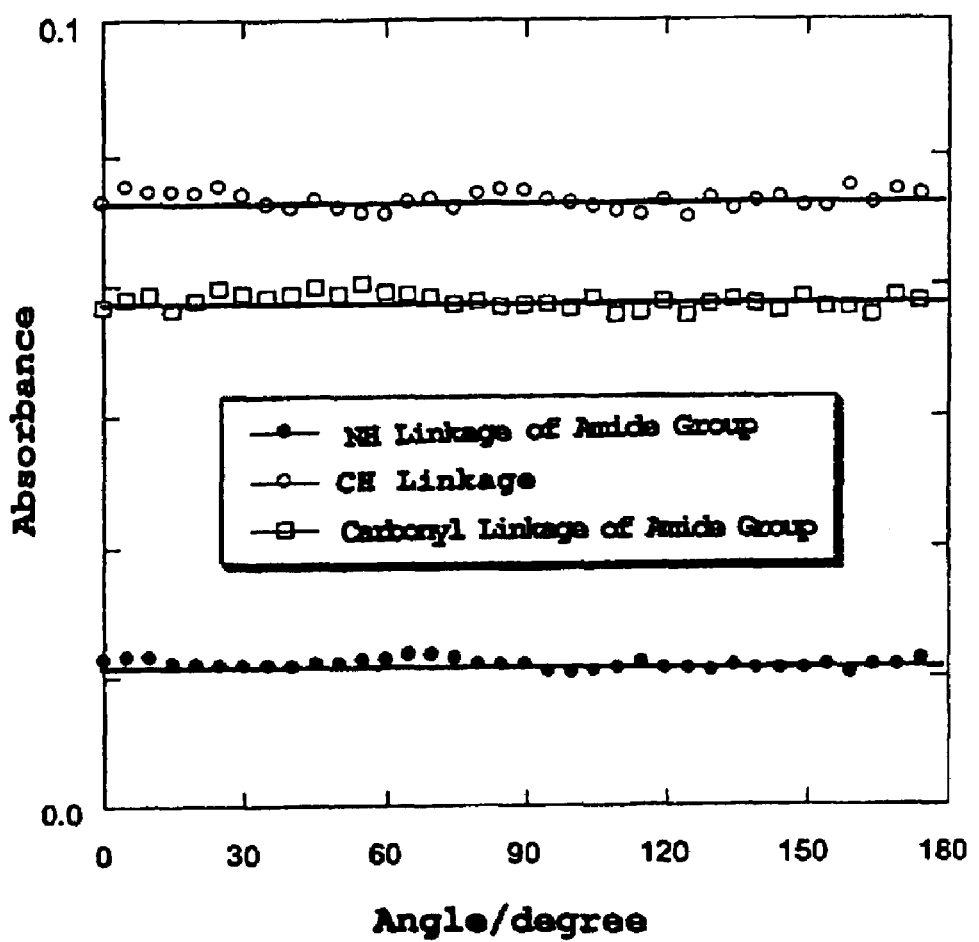
FIG. 12 shows an intensity distribution measured along the Debye ring of reflection derived from a distance between polymer chains of the polymer L1 (Example 5) of the present invention.

The photograph of X-ray is shown in FIG. 11 and diffraction pattern observed and the intensity distribution measured along the Debye ring of reflection derived from a distance between polymer chains is shown in FIG. 12, respectively. From FIG. 11 and FIG. 12, the practical standard value of parallelism degree in orientation was calculated as 0.92.

EXAMPLE 6

Synthesis of 4-ethynylbenzoyl-L-lactic Acid Decyl Ester as a Starting Monomer

Into a solution of 4-ethynylbenzoic acid (0.293 g, 2.01 mmol) in dimethylacetamide in a dry three-necked flask (100 mL), 4-dimethylaminopyridine (0.245 g, 2.01 mmol) and N,N'-dicyclohexylcarbodiimide (0.414 g, 2.01 mmol) were added and dissolved by stirring the mixture on an ice bath. L-decyllactic acid (0.462 g, 2.01 mmol) was added thereto, and the solution was stirred at room temperature for 3 hours. Then the solution was heated up to 120° C., followed by stirring for further 1 hour. After the solution was cooled to room temperature, precipitate was filtered off, and the product was isolated by column chromatography using silica gel.

EXAMPLE 7

Synthesis of Poly(4-ethynylbenzoyl-L-lactic Acid Decyl Ester): Polymer L2

[Chemical Formula 14]

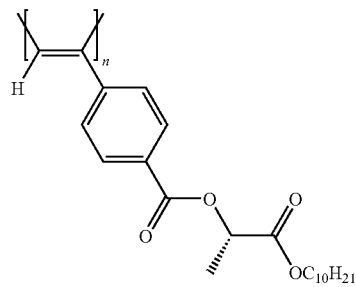

(Chemical Formula of Polymer L2)

In a dry polymerization tube (50 ml), 4-ethynylbenzoyl-L-lactic acid decyl ester (100 mg) as a starting monomer prepared in Example 6 was placed, and the tube was sufficiently deaerated, then purged with argon gas. After that, anhydrous THF (300 μL) and anhydrous triethylamine (100 μL) were added and dissolved by stirring. Then, a solution (56 μL) of bis(norbornadiene) rhodium dichloride (11.5 mg, produced by Aldrich Corp.) in anhydrous THF (1 mL) was added to said monomer solution, and the reaction liquid was stirred at 30° C. for 3 hours under the nitrogen atmosphere to promote the reaction. After completion of the reaction, the reaction liquid was added dropwise to methanol, and the precipitate was obtained by centrifugation at 3,000 rpm. The solution of the precipitate in benzene was subjected to freeze dry to obtain poly(4-ethynylbenzoyl-L-lactic acid decyl ester) (Polymer L2). The number average molecular weight of the resulting polymer was about 350,000.

INDUSTRIAL APPLICABILITY

As described above, the liquid crystalline polyacetylene derivatives according to the present invention and solids in which the liquid crystal structure has been immobilized are widely applicable as optical materials, and applications, for example, to circularly polarizing filters for IR rays of 1,550 nm and 1,300 nm which are used for optical communication, variable retardation film, chemical substance recognition sensor and high-density recording device can be considered, and also these molecular elements can be produced simply at low cost without a large sized manufacturing facility.

What is claimed is:

1. A liquid crystal composition comprising a polyacetylene derivative that has an amino acid introduced into side chain thereof, wherein an amino acid having an ester linkage with $C_2$-$C_{22}$ alkyl group, or having an amide linkage with $C_2$-$C_{22}$ alkyl group, and whereby exhibiting hydrogen-bond-forming property, and that has a rigid-rod helical structure and exhibits a liquid crystal phase in a solution containing an organic solvent as a main component or in a molten state.

2. The liquid crystal composition according to claim 1, wherein the polyacetylene derivative has a rigid-rod molecular shape and exhibits a high degree of polymer chain orientation with application of an electric field in a solution or in a molten state thereof.

3. The liquid crystal composition according to claim 1, wherein the polyacetylene derivative forms hydrogen bond between the amide groups on the neighboring side chains.

4. The liquid crystal composition according to claim 1, wherein the polyacetylene derivative has a repeating unit represented by the following general formula [1]:

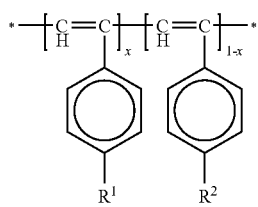

[1]

wherein each of $R^1$ and $R^2$ independently represents aminocarbonyl group of an amino acid having an ester linkage with $C_2$-$C_{22}$ alkyl group, or carbonylamino group of an amino acid having an amide linkage with $C_2$-$C_{22}$ alkyl group, said amino acid being achiral, either(S) chiral configuration or (R) chiral configuration, or a mixture composed of (8)- and (R)-antipodes; and X represents a number satisfying $0<X\leq 1$.

5. The liquid crystal composition according to claim 4, comprising the polyacetylene derivative represented by the general formula [1], wherein each of $R^1$ and $R^2$ is independently an aminocarbonyl group of an amino acid having an ester linkage with $C_2$-$C_{22}$ alkyl group.

6. The liquid crystal composition according to claim 4, comprising the polyacetylene derivative represented by the general formula [1] exhibiting polymerization degree of 30 or above.

7. The liquid crystal composition according claim 1, comprising the polyacetylene derivative of which viscosity index measured at 30° C. is 0.8 or above.

8. The liquid crystal composition according claim 1, comprising the polyacetylene derivative of which persistence length is 10 nm or above.

9. The liquid crystal composition according to claim 1, wherein the structure of liquid crystal phase is immobilized by evaporating a solvent.

10. The liquid crystal composition according to claim 9, wherein a form thereof is membranous.

* * * * *